United States Patent [19]
Park et al.

[11] Patent Number: 5,991,661
[45] Date of Patent: Nov. 23, 1999

[54] SYSTEM AND METHOD FOR MEASURING CARDIAC ACTIVITY

[75] Inventors: Euljoon Park, Stevenson Ranch; Gene A. Bornzin, Simi Valley; Joseph J. Florio, La Canada; Kerry Bradley, Pasadena, all of Calif.

[73] Assignee: Pacesetter, Inc., Sylmar, Calif.

[21] Appl. No.: 08/954,326

[22] Filed: Oct. 17, 1997

[51] Int. Cl.$^6$ .................................................. A61N 1/365
[52] U.S. Cl. ........................................................ 607/19
[58] Field of Search ................................. 607/9, 17, 19, 607/24, 25

[56] References Cited

U.S. PATENT DOCUMENTS

| | | | |
|---|---|---|---|
| 3,815,611 | 6/1974 | Denniston . | |
| 4,140,132 | 2/1979 | Dahl | 128/419 PG |
| 4,428,378 | 1/1984 | Anderson et al. | 128/419 PG |
| 4,708,143 | 11/1987 | Schroeppel | 128/419 PG |
| 4,774,950 | 10/1988 | Cohen | 128/419 D |
| 4,802,481 | 2/1989 | Schroeppel . | |
| 4,967,748 | 11/1990 | Cohen | 128/419 D |
| 5,014,700 | 5/1991 | Alt | 128/419 PG |
| 5,031,615 | 7/1991 | Alt | 128/419 PG |
| 5,040,534 | 8/1991 | Mann et al. | 128/419 PG |
| 5,040,535 | 8/1991 | Mann et al. | 128/419 PG |
| 5,044,366 | 9/1991 | Alt | 128/419 PG |
| 5,156,148 | 10/1992 | Cohen . | |
| 5,454,838 | 10/1995 | Vallana et al. | 607/19 |
| 5,480,412 | 1/1996 | Mouchawar et al. | 607/6 |
| 5,549,650 | 8/1996 | Bornzin et al. . | |
| 5,562,711 | 10/1996 | Yerich et al. . | |
| 5,674,256 | 10/1997 | Carlson | 607/17 |
| 5,836,987 | 11/1998 | Baumann et al. | 607/17 |

OTHER PUBLICATIONS

Atochem Sensors, Inc., "Kynar Piezo Film," *Standard and Custom Piezo Film Components*, pp. 1–12.

Salerno, David M. M.D., Ph.D et al., "Seismocardiography for Monitoring Changes in Left Ventricular Function during Ischemia," *Chest*/100/4/Oct. 1991.

Salerno, David M. M.D., Ph.D et al., "Seismocardiographic Changes Associated with Obstruction of Coronary Blood Flow Furing Balloon Angioplasty," *The American Journal of Cardiology*, vol. 68, pp. 201–207 (Jul. 15, 1991).

Sandler, H. et al., "Miniature Implantable Accelerometers," pp. 165–174.

Piezo Electric Products, Inc., "Piezoceramic Design Notes," *Sensors* (6 pp) (Mar. 1984).

Bacharach, David W. et al., "Activity–Based Pacing: Comparison of a Device Using an Accelerometer Versus a Piezoelectric Crystal," *PACE*, vol. 15, pp. 188–196 (Feb. 1992).

Ovsyshcher, Ilya et al., "First Derivative of Right Ventricular Pressure, dP/dt, as a Sensor for a Rate Adaptive VVI Pacemaker: Initial Experience," *PACE*, vol. 15, pp. 211–218 (Feb. 1992).

Salerno, David M. et al., "Seismocardiography: A New Technique for REcording Cardiac Vibrations. Concept, Method, and Initial Observations," *Journal of Cardiovascular Technology*, vol. 9, No. 2, 1990, pp. 111–118.

*Primary Examiner*—Jeffrey R. Jastrzab

[57] ABSTRACT

An implantable cardiac stimulation device, such as a pacemaker or an implantable cardioverter-defibrillator, that includes an accelerometer-based activity sensor that processes one or more signals from the activity sensor to obtain parameters that are indicative of the heartbeat of the patient. The implantable cardiac stimulation device determines when the patient is at rest and the activity sensor provides a signal that corresponds to the acceleration of the sensor due to the heartbeat of the patient. This acceleration signal is integrated over time once to provide a contractility parameter, which is indicative of the contractility of the heart and is integrated over time twice to provide a displacement parameter, which is indicative of the displacement of the heart wall during the heartbeat. This displacement parameter is thereby indicative of the volume of blood pumped by the heart. A microprocessor uses either the contractility parameter, the displacement parameter or both to modify the delivery of therapeutic stimulation pulses to the heart.

23 Claims, 5 Drawing Sheets

5,991,661

SYSTEM AND METHOD FOR MEASURING CARDIAC ACTIVITY

FIELD OF THE INVENTION

The present invention relates to implantable cardiac stimulation devices, such as pacemakers and implantable cardioverter-defibrillators and, in particular, concerns a system and method for measuring cardiac activity using an accelerometer that is positioned within a pacemaker or ICD case.

BACKGROUND OF THE INVENTION

Implantable cardiac stimulation devices are commonly used to provide therapy to regulate the functioning of the heart. These types of devices include pacemakers and implantable cardioverter-defibrillators (ICD). These devices have become more versatile since their original development as these devices are better able to regulate the function of the heart to optimize the performance of the heart to meet the patient's current needs.

In particular, the more sophisticated pacemakers include sensors, which are capable of sensing the function of the heart and the activity level of the patient. This information is then used to adjust pacing parameters so that the heart is regulated to beat in the optimum manner for the particular patient given the sensed conditions. A typical method of determining the activity level of the patient is to position an accelerometer within the housing that contains the control unit for the implantable cardiac stimulation device. The housing is generally positioned within the body of the patient, e.g., under the pectoral muscle for a pectoral implant device, and the accelerometer provides a signal which is indicative of the level of activity of the patient.

The function of the heart is quite often monitored through one or more of the leads that are positioned within the chambers of the heart which provide an intracardiac electrogram (IEGM) signal to the controller that controls the operation of the implantable cardiac stimulation device. The IEGM therefore provides a signal to the controller, which is indicative of the frequency at which the heart is beating. The controller can then use the IEGM signal and the activity signal provided by the activity sensor to ascertain when and how electrical stimulation pulse therapy should be provided to the heart to optimize the function of the heart for the activity level of the patient. The controller can also use the IEGM signal to detect the occurrence of arrhythmias, which would necessitate the delivery of anti-tachycardia stimulation pulses, low or high amplitude shocks to convert the arrhythmia.

While the IEGM provides an indication as to the heart rate, the IEGM does not generally provide the controller with an indication as to the volume of blood being pumped by the heart. It is understood that the amount of blood being pumped by the heart is a factor not only of the heart rate, but also of the stroke volume of the heart. To optimize the hemodynamics of the heart, it is generally preferable that the largest volume of blood be pumped for a given heart rate. Hence, it is desirable that the controller receive some sort of signal as to the contractility or displacement of the heart which can then be used as a basis for determining the hemodynamic efficiency of the heart.

One such device is disclosed in U.S. Pat. No. 5,549,650 wherein an accelerometer is positioned within a lead that is located within one of the chambers of the heart. Preferably, this lead is attached to one of the walls of the heart so that movement of the wall of the heart is sensed by the accelerometer. The accelerometer then sends a signal to the controller, which is integrated twice. The integration of the lead accelerometer signal results in both a first signal indicative of the contractility of the heart and also a second signal, which is indicative of the physical displacement of the wall of the heart. This information can then be used by the controller to adjust the pacing parameters of the implanted device to improve the hemodynamic efficiency of the heart as this information is directly related to the volume of blood being pumped by the heart during each heartbeat.

While U.S. Pat. No. 5,549,650 discloses a device that is capable of providing information to a controller as to the volume of blood pumped during each heartbeat, it will be appreciated that mounting an accelerometer in a lead that is attached to one of the walls of the heart is both invasive and expensive. With many patients, the therapeutic benefit provided by the sensor disclosed in U.S. Pat. No. 5,549,650 would not be justified in light of the invasiveness and cost of mounting the sensor on the inner wall of the patient's heart. For these patients, the system disclosed in U.S. Pat. No. 5,549,650 does not provide a suitable solution for providing the controller with additional information to optimize the hemodynamic efficiency of the heart.

From the foregoing, it should be apparent that there is a need for a system that will provide information to the controller of an ICD or pacemaker relating to the hemodynamic performance of a patient's heart without requiring any additional implantation of hardware within the patient. In particular, there is a need for a device that will provide information about the contractility and displacement of the heart without requiring the implantation of an additional sensor within the heart of the patient.

SUMMARY OF THE INVENTION

The aforementioned needs are satisfied by the implantable cardiac stimulation device of the present invention which is comprised of a control means, one or more leads that are coupled to the control means and are positioned within the chambers of the heart, and an activity sensor which is comprised of an accelerometer located in the house that provides signals to the control means indicative of the activity level of the patient. Preferably, the control means is configured to be able to determine, based on signals from the activity sensor, when the patient is at rest. Furthermore, when the patient is at rest, the control means receives signals from the accelerometer-based activity sensor which are representative of either the contractility or the displacement of the patient's heart.

Advantageously, Applicant has determined that with an accelerometer-based activity sensor that is mounted within the case of an implantable cardiac stimulation device, where the case is implanted adjacent the chest of the patient, the accelerometer provides a detectable acceleration signal following the occurrence of a QRS complex (or stimulating pulse) when the patient is at rest. This detectable acceleration signal occurs as a result of the sensor moving due to the displacement of the walls of the heart during a heartbeat. The Applicant has further determined that by integrating this acceleration signal a first time, the resultant first integration signal is indicative of the contractility of the heart. Further, the Applicant has also determined that a second integration of the acceleration signal provided by the accelerometer-based activity sensor is indicative of the total displacement of the heart wall of the patient.

Consequently, the acceleration signal from the activity sensor is integrated over time so as to obtain a contractility parameter and/or a displacement parameter. These parameters can then be used by the control means to regulate the delivery of therapeutic electrical stimulation pulses to the heart via the leads to improve hemodynamic efficiency of the heart.

In another aspect of the present invention, a method for providing therapeutic electrical stimulation pulses to the heart is provided. The method is comprised of determining when the patient is at rest, obtaining an acceleration signal of the heart from an activity sensor positioned within a housing, or case, that contains the controller of an implantable cardiac stimulation device, and then integrating the acceleration signal one or more times to obtain contractility and/or displacement signals. The contractility and/or displacement signals can then be used to alter the delivery of therapeutic electrical stimulation pulses to the heart via leads positioned within the heart chambers to optimize the hemodynamic efficiency of the heart. These and other objects and advantages of the present invention will become more fully apparent from the following description taken in conjunction with the accompanying claims.

DETAILED DESCRIPTION OF THE PREFERRED EMBODIMENT

Figure 1:
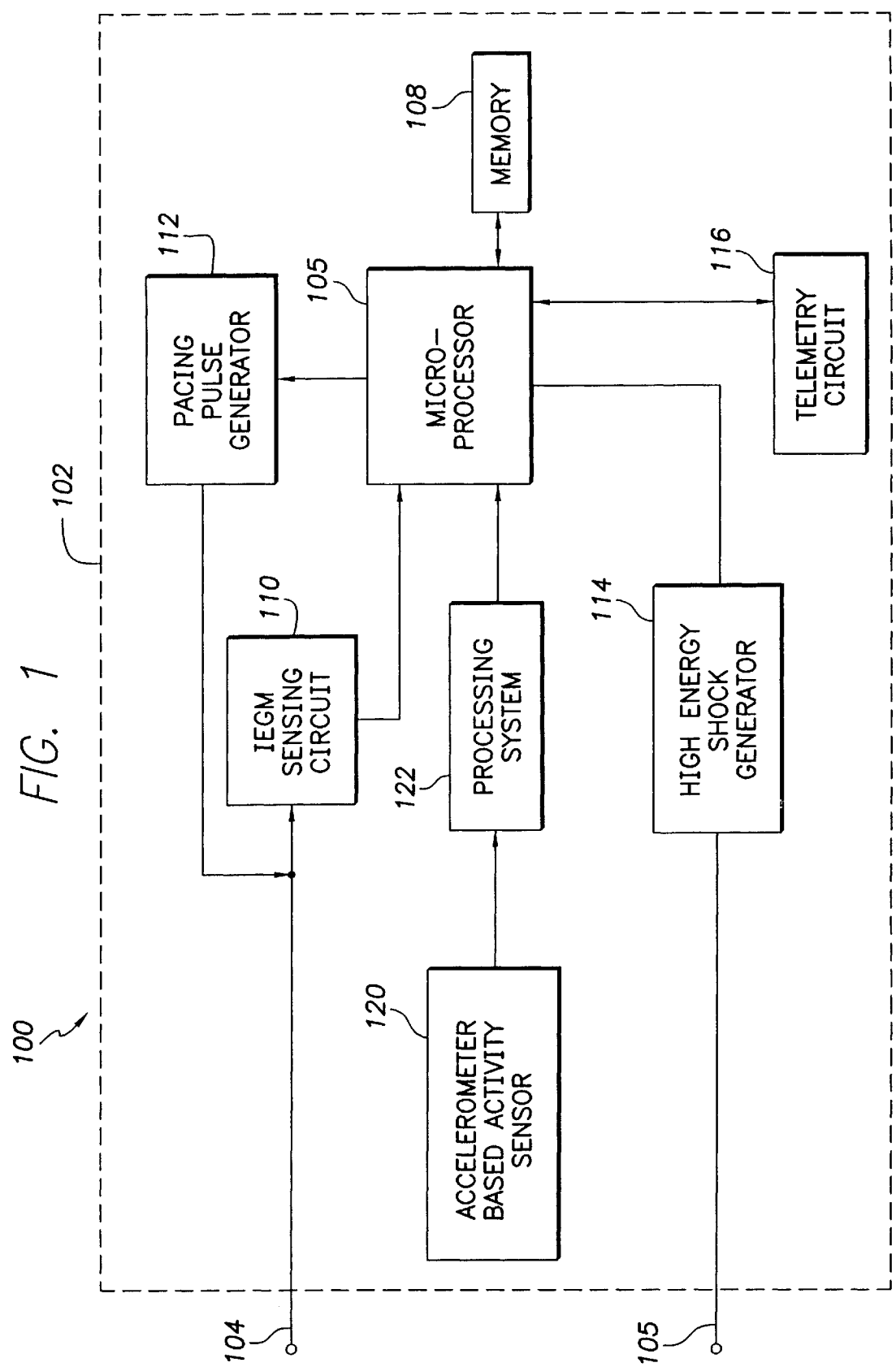
FIG. 1 is a schematic illustration of an implantable cardiac stimulation device that can be implanted within a patient for regulation of the function of the patient's heart.

Reference will now be made to the drawings wherein like numerals refer to like parts throughout. FIG. 1 illustrates an implantable cardiac stimulation device 100, such as a pacemaker or ICD that is implanted within the body of a patient (not shown). The device 100 includes control circuitry 102 that is typically positioned within a housing (not shown) that is implanted within the body of the patient. One typical method of implantation is called pectoral implantation wherein the case containing the control circuitry 102 is implanted underneath the pectoral muscle of the patient. The device 100 includes one or more leads 104 which are implanted into the chambers of the heart, while being connected to the control circuitry 102, in a manner that is well known in the art.

The control circuitry 102 includes a controller or microprocessor 106 which induces the device 100 to apply therapeutic stimulation pulses to the heart via the leads 104 and 105 in response to sensed conditions and based upon instructions that are stored within a memory 108. In particular, the device 100 includes an IEGM sensing circuit 110, which provides an intracardiac electrogram (IEGM) signal to the microprocessor 106. The IEGM sensing circuit 110 obtains the IEGM signal from the lead 104 that is preferably positioned within the right ventricle of the heart in a manner that is well known in the art. The lead 104 may in fact be a pacing lead that is implanted in the apex of the right ventricle of the heart.

The microprocessor 106 induces a pacing pulse generator 112 to apply pacing pulses to the heart in response to the conditions sensed by the IEGM sensing circuit 110. Similarly, this embodiment of the implantable cardiac stimulation device 100 also has a high energy shock generator 114 which is capable of providing a cardioversion or defibrillation shock to the heart via the lead 105. The operation of the microprocessor 106, the pacing pulse generator 112, the IEGM sensing circuit 110 and the high energy shock generator 114 is similar to the operation of similar devices in prior art implantable cardiac stimulation devices. The microprocessor 106 is also capable of exchanging information with an external monitor via a telemetry circuit 116 in a manner that is also well known in the art.

As is also shown in FIG. 1, the preferred embodiment of the control circuitry 102 includes an accelerometer-based activity sensor 120. This activity sensor 120 monitors the activity level of the patient and provides a signal to the microprocessor 106 via a processing system 122 that is indicative thereof. The activity sensor 120 is preferably comprised of an accelerometer, which measures the acceleration on the sensor 120 resulting from movement. Body movement of the patient will result in a high amplitude signal from the accelerometer. Advantageously, contractions of the heart may also be sensed by the activity sensor 120 and will result in a low amplitude signal superimposed with the high amplitude body motion signal. By amplifying the accelerometer signal during periods when the patient is at rest, the low amplitude signal may be obtained from the accelerometer. The microprocessor 106 can then use the low amplitude signal to alter the delivery of therapeutic stimulation pulses to the heart.

For example, the activity sensor preferably provides a signal to the microprocessor 106 that indicates the patient is undergoing heightened physical exertion. At this point, the microprocessor 106 can induce the pacing pulse generator 112 to increase the base pacing rate so that the heart provides a sufficient amount of blood to accommodate the increased activity level of the patient. Conversely, when the activity sensor 120 senses a decreased level of activity of the patient, the microprocessor can induce the pacing pulse generator circuit 112 to deliver pacing pulses at a lower pacing rate.

The accelerometer-based activity sensor 120 of the preferred embodiment is similar to the accelerometer-based activity sensors used in the prior art and, in particular, is substantially identical to the accelerometer-based activity sensor that is currently used in the Trilogy® and Affinity™ pacemakers that are currently manufactured by Pacesetter®, Inc. of Sylmar, Calif.

Figure 2:
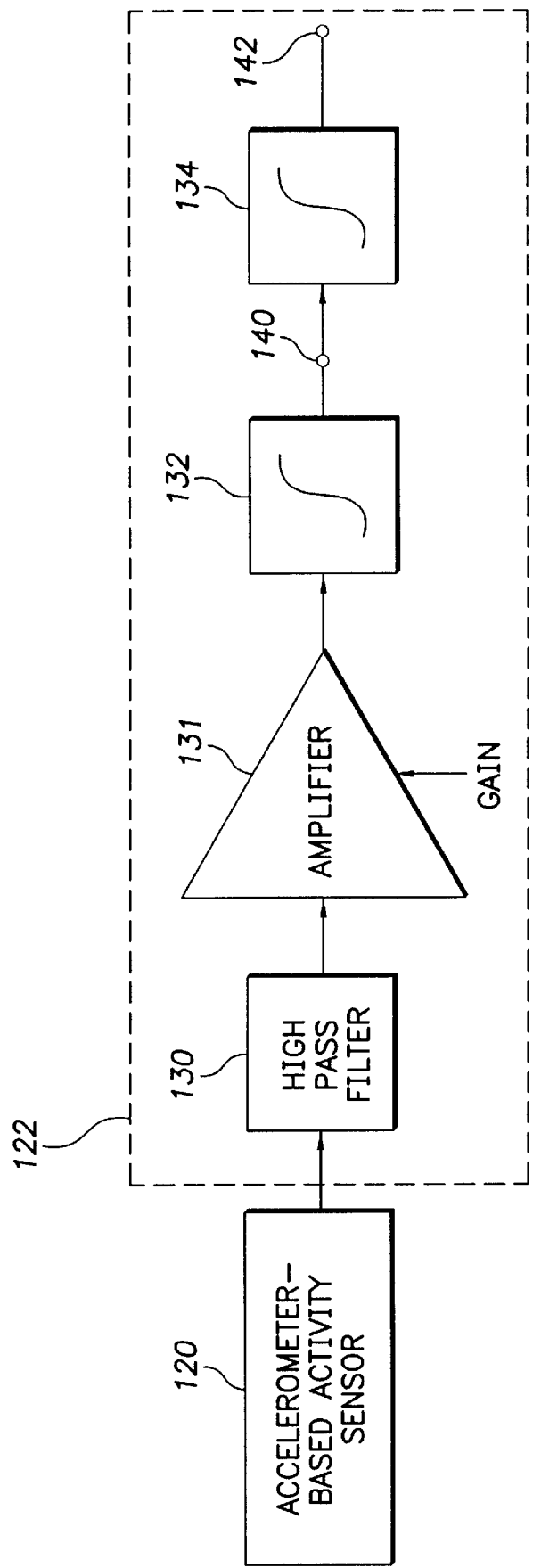
FIG. 2 is a functional block diagram of a processing system that receives a signal from an accelerometer-based activity sensor and integrates the signal one or more times so as to output contractility and displacement parameter signals to the microprocessor of the implantable cardiac stimulation device shown in FIG. 1.

Advantageously, the processing system 122 could be configured to process the activity signal provided by the activity sensor 120 so as to provide the microprocessor 106 with an indication as to the contractility and displacement of the heart. In particular, as shown in FIG. 2, the signal produced by the activity sensor 120 can be provided to a high pass filter 130, which rejects unwanted signals, such as DC offset. An amplifier 131, having automatic gain control, amplifies the filtered signal. If the signal is above a predetermined threshold (i.e., the patient is exercising), then the gain of the amplifier 131 is decreased, or optimized, so that the body motion signals corresponding to various levels of exercise can be detected. If the signal is below a predetermined threshold (i.e., the patient is at rest), then the amplifier 131 is set to a high gain to detect the low amplitude motion signals corresponding to contractions of the heart. The amplified motion signal is then provided to a first integrator 132. The first integrator 132 integrates the acceleration signal and thereby provides a contractility or velocity signal at node 140. The contractility signal 140 is then provided to a second integrator 134, which then provides a signal that is indicative of the displacement of the heart.

As will be explained in greater detail hereinbelow, it has been determined that the accelerometer, as is used for activity sensing in a typical implantable cardiac stimulation device that is positioned within the housing of the device, produces an acceleration signal that corresponds to the movement of the heart during each heartbeat. By supplying this signal to the processing system 122, a contractility signal and a displacement signal can be provided at nodes 140 and 142, respectively, which are indicative of the contractility and displacement of the heart.

Applicant has, however, determined that in the embodiment described herein, the patient must be at rest to obtain the contractility signal 140 or the displacement signal 142 using the activity sensor accelerometer 120. Otherwise, the body movement of the patient results in the activity sensor 120 providing sufficient signals to the processing system 122 such that the amplitude of the acceleration signal corresponding to the heartbeat is masked.

Figure 3:
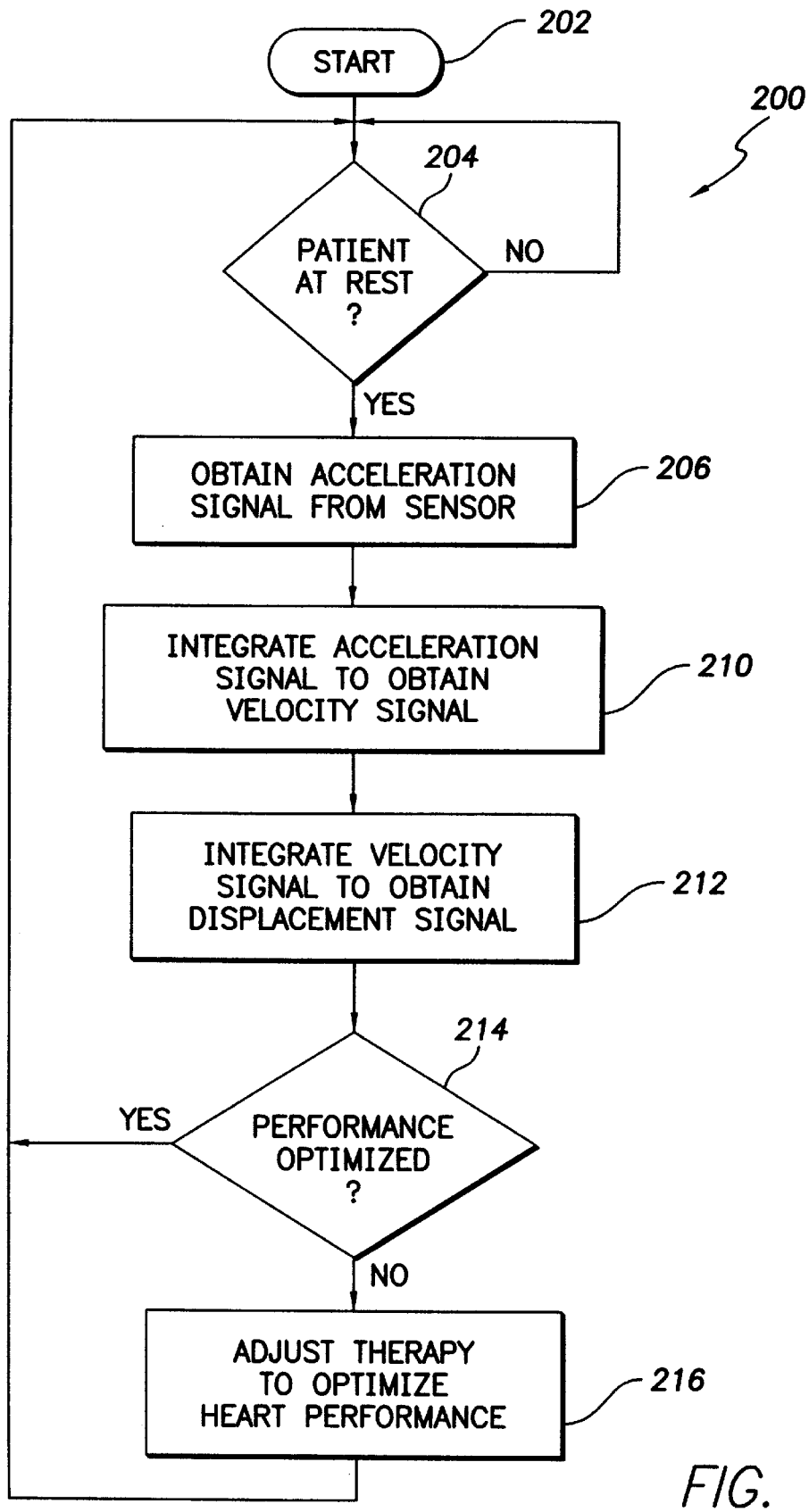
FIG. 3 is a flowchart illustrating the exemplary operation of the implantable cardiac stimulation device shown in FIG. 1 as it obtains a contractility and displacement parameters.

FIG. 3 is a flowchart, which illustrates an exemplary program implemented by the microprocessor 106 in order to obtain the contractility and displacement signals 140, 142. A person of ordinary skill in the art will appreciate that the blocks in FIG. 3 are simply representative of the functional steps performed by the microprocessor 106 to implement the process described herein and that the actual steps and procedures used by the microprocessor used to implement the process may, in fact, vary depending upon the implementation.

In the flowchart 200, the microprocessor 106 begins at a start state 202 and then proceeds to determine in decision state 204 whether the patient is at rest. As discussed above, the activity sensor 120 is providing signals to the microprocessor 106, which are indicative of the activity of the patient. In the event that the patient is active, the signals that are being provided by the activity sensor 120, in this embodiment, will generally mask any acceleration signals that correspond to the heartbeat of the patient. Consequently, in this embodiment, the microprocessor 106 initially determines whether the patient is at rest.

This determination can be made by reviewing the signals being provided by the activity sensor 120 to determine whether they correspond to a higher activity level of the patient above a predetermined threshold value. Alternatively, the implantable cardiac stimulation device 100 may also be equipped with a position switch, such as the position switch used in U.S. Pat. No. 5,549,650, which provides an indication as to whether the patient is lying down in a supine position.

In the event that the microprocessor 106 determines that the patient is at rest, the microprocessor 106 then proceeds to obtain, in state 206, an acceleration signal from the activity sensor 120. In the preferred embodiment, the only source of acceleration on the activity sensor 120 positioned within the case mounted adjacent the patient's chest wall is the contraction of the heart. Hence, the acceleration signal sensed by the activity sensor during this interval is representative of the acceleration of the sensor due to the displacement of the heart. While in the preferred embodiment the acceleration signal of the heart is only obtained when the patient is at rest, it will be appreciated that further processing of the signals from the activity sensor 120 may result in the ability to distinguish the acceleration signal corresponding to the heartbeat even when the patient is not at rest.

The acceleration signal detected by the activity sensor 120 is then integrated over time in state 210 to provide the contractility signal 140 (FIG. 2). The integration can either be performed using a hardware integrator, such as the integrator disclosed in U.S. Pat. No. 5,549,650, or the microprocessor 106 can incorporate software which will mathematically integrate over time the acceleration signal provided by the activity sensor 120.

Subsequently, the contractility signal 140 is then integrated over time in state 212 to provide the displacement signal 142 again either using a hardware or software integrator. The microprocessor 106 can then use the contractility signal 140 and the displacement signal 142 provided by the activity sensor 120 to change or optimize the hemodynamic performance of the heart. These signals can be used to regulate the base rate, AV delay or other pacing parameters so that the heart is paced at a rate whereby an optimum amount of blood is being pumped by the heart to meet the resting conditions of the patient.

Hence, in the preferred embodiment, the microprocessor 106 determines, in decision state 214, whether the performance of the heart is optimized for the sensed conditions. In the event that the performance of the heart is optimized, the microprocessor then returns to the loop comprising the states 204 through 214. In the event that the performance of the heart is not optimized for the particular conditions, the microprocessor 106 then alters one of the therapeutic parameters of the implantable cardiac stimulation device in state 216 to optimize the heart performance.

It will be appreciated that the altering of the therapeutic parameters may comprise altering the base rate, altering the AV delay or any of another number of parameters that are adjustable by the microprocessor 106 when providing therapeutic stimulation pulses to the heart. In this way, the microprocessor 106 can use an acceleration signal detected by the activity sensor 120 when the patient is at rest to alter the delivery of therapeutic stimulation pulses to the heart so that heart function is regulated for the given sensed condition. It will be appreciated, of course, that the exact manner in which the performance of the implantable electric device is altered as a result of the sensed conditions may vary depending upon the type of implantable cardiac stimulation device positioned within the patient, the condition of the patient and a variety of other factors that are well known in the art.

Figure 4:
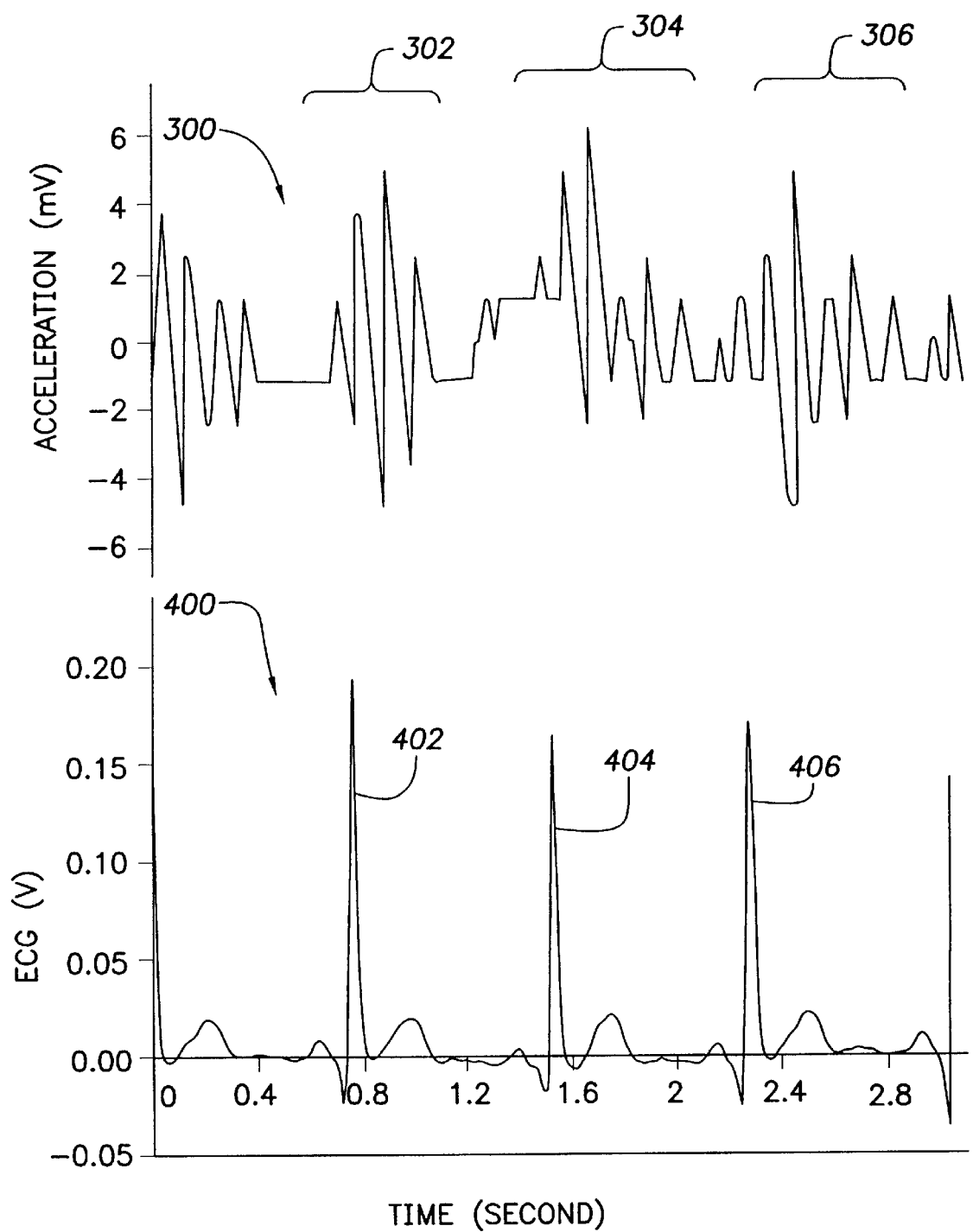
FIG. 4 is a diagram which illustrates that an activity sensor is capable of detecting an acceleration signal corresponding to movement of the heart during a heartbeat.

FIG. 4 is a reproduction of a simultaneous recording of an ECG and an acceleration signal sent by an activity sensor, such as the sensor 120 that corresponds to the occurrence of a heartbeat. In particular, a pacemaker case, which includes an accelerometer-based activity sensor, such as the sensor described above, was taped to a patient's chest and an ECG of the patient was also obtained in a conventional manner. In FIG. 4, the top trace 300 of the acceleration signal measured by the accelerometer and the bottom trace 400 is the corresponding ECG signal. As shown in FIG. 4, the acceleration signal oscillates right after each QRS complex. In FIG. 4, this oscillation is identified by the reference numerals 302, 304 and 306. The corresponding QRS complexes in FIG. 4 are identified as 402, 404 and 406. Hence, when the patient is at rest, the accelerometer in the activity sensor is capable of detecting the acceleration of the housing that contains the activity sensor that is the result of the patient's heartbeat. This acceleration signal can then be integrated in the manner described above so that a contractility and displacement signal can be produced.

Figure 5:
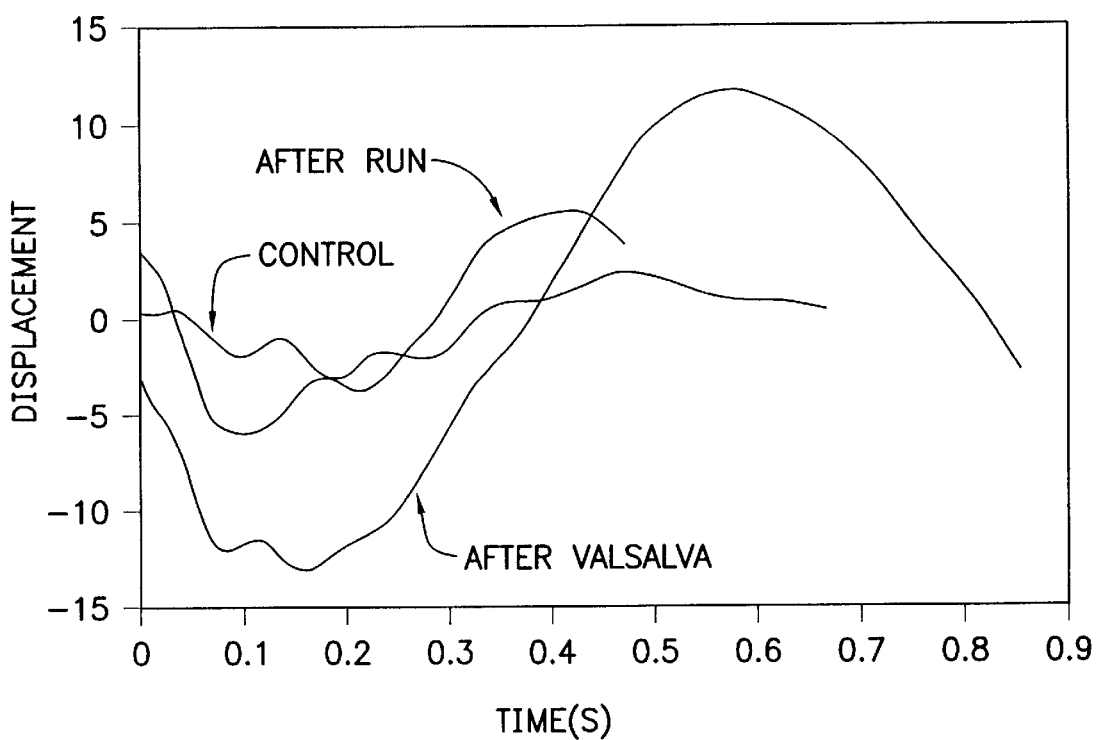
FIG. 5 is a diagram that illustrates the calculated displacement of the heart wall using a system corresponding to the system of FIG. 1.

FIG. 5 illustrates the displacement of the heart wall using the activity-based accelerometer that was taped to the chest of the patient as described with reference to FIG. 4. The cardiac acceleration was investigated by performing some brief hemodynamic maneuvers. In particular, a control signal was obtained wherein the patient was at rest and had a heart rate of 90 beats per minute. The peak-to-peak displacement of the activity sensor was 5.6 in arbitrary units. Immediately after running, the measured heart rate of the resting patient was 127 beats per minute and the peak-to-peak displacement of the activity sensor was 11.7 in arbitrary units. Similarly, after a Valsalva maneuver, the heart rate of the patient was 70 and the peak-to-peak displacement of the activity sensor was 25 in arbitrary units, which (as expected) occurs as a result of the huge surge in venous return following the maneuver. It will be appreciated that FIG. 5 illustrates that the activity sensor used in Applicant's experiments was capable of providing a parameter, which is highly indicative of the displacement of the heart under various observed conditions.

Consequently, the system and method of the preferred embodiment allows for the measurement of a displacement parameter and a contractility parameter of the heart wall. This provides a good hemodynamic indicator when the patient is at rest. Further, this hemodynamic indicator is provided without requiring the implantation of an additional sensor into the patient. Consequently, this system and method is particularly suitable for patients wherein the net benefit of implanting an additional sensor to detect displacement or contractility of the heart is not warranted in light of the heightened risk and cost. The system and method of the preferred embodiment is capable of providing a signal that is indicative of the displacement of the heart when the patient is a rest without the addition of additional implanted hardware.

Although the foregoing description of the preferred embodiments of the present invention have shown, described and pointed out the fundamental novel features of the invention, it will be understood that various omissions, substitutions and changes in the form of the detail of the apparatus as illustrated, as well as the uses thereof, may be made by those skilled in the art without departing from the spirit of the present invention. Consequently, the scope of the present invention should not be limited to the foregoing discussion, but should be defined by the appended claims.

What is claimed is:

1. An implantable cardiac stimulation device having a hermetically sealed housing, the device comprising:

pulse generating means for generating therapeutic stimulation pulses to a patient's heart;

sensing means, mounted within the housing, for sensing acceleration of the cardiac wall resulting from the patient's heartbeat and for providing a cardiac wall acceleration signal indicative thereof;

means for integrating the cardiac wall acceleration signal twice to produce a cardiac wall displacement signal; and control means, coupled to the pulse generating means and the integrating means, for controlling the delivery of the therapeutic stimulation pulses to the patient's heart and for altering the delivery of therapeutic stimulation pulses based, at least in part, on the cardiac wall displacement signal.

2. The implantable stimulation device of claim 1, wherein:

the sensing means includes means for sensing an activity level of the patient and for providing a body acceleration signal indicative thereof; and the control means includes means for altering the delivery of therapeutic stimulation pulses based, at least in part, on the body acceleration signal.

3. The implantable stimulation device of claim 2, wherein:

the integrating means includes means for integrating the cardiac wall acceleration signal over time to produce a cardiac wall velocity signal corresponding to a contractility parameter of the heart; and the control means includes means for altering the delivery of therapeutic stimulation pulses to the heart based upon the cardiac wall velocity signal.

4. The implantable stimulation device of claim 3, wherein the control means further comprises:

means for determining when the patient is at rest based on the body acceleration signal; and means for triggering the integrating means to determine the cardiac wall velocity signal when the patient is at rest.

5. The implantable stimulation device of claim 1, wherein the control means further comprises:

means for determining when the patient is at rest based on the body acceleration signal; and means for triggering the integrating means to determine the cardiac wall displacement signal when the patient is at rest.

6. A method of regulating the delivery of therapeutic electrical stimulation pulses to a patient's heart from an implantable cardiac stimulation device having a housing with an accelerometer-based sensor mounted therein, the method comprising the steps of:

sensing a first acceleration signal corresponding to the mechanical contraction of the heart with the accelerometer-based sensor mounted in the housing;

processing the first acceleration signal to produce a cardiac wall displacement signal which is indicative of the volume of blood provided by the heart during a single heartbeat;

providing a first control signal based on the cardiac wall displacement signal; and modifying the delivery of therapeutic stimulation pulses to the heart based, at least in part, on the first control signal.

7. The method of claim 6, further comprising the steps of:

sensing a second acceleration signal corresponding to a physical activity level of the patient;

providing a second control signal based on the second acceleration signal; and modifying the delivery of therapeutic stimulation pulses to the heart based, at least in part, on the second control signal.

8. The method of claim 7, further comprising the steps of:

determining whether the patient is at rest based on the second acceleration signal; and modifying the delivery of therapeutic stimulation pulses to the heart based, at least in part, on the first control signal when the patient is at rest.

9. The method of claim 8, further comprising the steps of:
   integrating the first acceleration signal over time to produce a cardiac wall velocity signal that corresponds to a contractility parameter of the heart; and
   providing a third control signal based on the cardiac wall velocity signal.

10. The method of claim 7, wherein the step of modifying the delivery of therapeutic stimulation pulses to the heart further comprises the step of:
   adjusting the rate of the stimulation pulses based on at least one of the first and second control signals.

11. The method of claim 7, wherein the step of modifying the delivery of therapeutic stimulation pulses to the heart further comprises the steps of:
   generating stimulation pulses in the patient's atrium and in the patient's ventricle, the stimulation pulses being separated by an A–V Delay interval; and
   adjusting the A–V Delay interval based on the first control signal.

12. The method of claim 6, wherein the step of modifying the delivery of therapeutic stimulation pulses comprises the step of:
   modifying the delivery of therapeutic stimulation pulses to optimize the performance of the heart so that a maximum volume of blood is pumped by the heart during each heartbeat.

13. An implantable cardiac stimulation device having a hermetically sealed housing, the device comprising:
   pulse generating means for generating therapeutic stimulation pulses to a patient's heart;
   sensing means, mounted within the housing, for sensing acceleration and for providing an acceleration signal indicative thereof;
   detection means for detecting a low amplitude component of the acceleration signal corresponding to heart wall acceleration resulting from the patient's heartbeat;
   integrating means for integrating the low amplitude component of the acceleration signal twice to produce a first control signal corresponding to a physical displacement of the cardiac wall of the heart; and
   control means, coupled to the pulse generating means and the integrating means, for controlling the delivery of the therapeutic stimulation pulses to the patient's heart and for altering the delivery of therapeutic stimulation pulses based, at least in part, on the first control signal.

14. The implantable stimulation device of claim 13, wherein:
   the detection means includes means for detecting a high amplitude component of the acceleration signal corresponding to an activity level of the patient; and
   the control means includes means for altering the delivery of therapeutic stimulation pulses based, at least in part, on the high amplitude component of the acceleration signal.

15. The implantable stimulation device of claim 14, wherein the sensing means comprises:
   an accelerometer-based activity sensor that is responsive to both the acceleration of the heart wall due to the contraction of the heart and to body motion.

16. The implantable stimulation device of claim 13, further comprising:
   means for integrating the low amplitude component of the acceleration signal over time to produce a second control signal corresponding to a contractility parameter of the heart; and
   wherein the control means includes means for altering the delivery of therapeutic stimulation pulses to the heart based upon the second control signal.

17. The implantable stimulation device of claim 16, wherein the control means further comprises:
   means for determining when the patient is at rest based on the high amplitude component of the acceleration signal; and
   means for triggering the integrating means to integrate the low amplitude component of the acceleration signal when the patient is at rest.

18. The implantable stimulation device of claim 13, wherein the control means further comprises:
   means for determining when the patient is at rest based on the high amplitude component of the acceleration signal; and
   means for triggering the integrating means to twice integrate the low amplitude component of the acceleration signal when the patient is at rest.

19. The implantable stimulation device of claim 13, wherein the housing is of the type which is implantable beneath the pectoral muscle of the patient.

20. An implantable cardiac stimulation device having a hermetically-sealed housing, the device comprising:
   an accelerometer, mounted within the housing, that senses acceleration of the cardiac wall resulting from a patient's heartbeat, the accelerometer producing a cardiac wall acceleration signal as an output;
   signal processing circuitry, coupled to the accelerometer, that integrates the cardiac wall acceleration signal twice to produce a cardiac wall displacement signal;
   a pulse generator circuit that generates stimulation pulses to the patient's heart in response to a trigger signal which defines a timing between the stimulation pulses; and
   a control circuit, coupled to the pulse generator circuit and the signal processing circuitry, configured to modulate the timing of the stimulation pulses in response to the cardiac wall displacement signal.

21. The implantable stimulation device of claim 20, wherein:
   the signal processing circuitry further comprises:
      circuitry for processing the accelerometer to determine a body acceleration signal due to body motion of the patient during exercise;
      a detection circuit for determining when the patient is at rest and when the patient is exercising based on the body acceleration signal; and
   the control circuit modulates the timing of stimulation pulses based on the body acceleration signal when the patient is exercising and further modulates the rate of stimulation pulses based on the cardiac wall displacement signal when the patient is at rest.

22. The implantable stimulation device of claim 21, wherein:
   the timing of the stimulation pulses includes a base rate timing; and
   the control circuit further includes circuitry to determine an optimal base rate timing of stimulation pulses.

23. The implantable stimulation device of claim 21, wherein:
   the timing of the stimulation pulses includes an A–V timing; and the control circuit further includes circuitry to determine an optimal A–V timing of stimulation pulses.

* * * * *